(12) United States Patent
Augustine et al.

(10) Patent No.: US 7,277,177 B2
(45) Date of Patent: Oct. 2, 2007

(54) SYSTEM AND METHOD FOR CONTROLLING A LIGHT SOURCE FOR CAVITY RING-DOWN SPECTROSCOPY

(75) Inventors: Robert Augustine, Willow Grove, PA (US); Calvin R. Krusen, Richboro, PA (US); Chuji Wang, Hatboro, PA (US); Wen-Bin Yan, Cranbury, NJ (US)

(73) Assignee: Tiger Optics, LLC, Warrington, PA (US)

( * ) Notice: Subject to any disclaimer, the term of this patent is extended or adjusted under 35 U.S.C. 154(b) by 13 days.

(21) Appl. No.: 11/252,128

(22) Filed: Oct. 17, 2005

(65) Prior Publication Data
US 2006/0087655 A1 Apr. 27, 2006

Related U.S. Application Data

(63) Continuation-in-part of application No. 10/145,209, filed on May 13, 2002, now abandoned.

(51) Int. Cl.
*G01N 21/61* (2006.01)
(52) U.S. Cl. .................... 356/437; 250/343
(58) Field of Classification Search ........... 356/437, 356/440; 250/343
See application file for complete search history.

(56) References Cited

U.S. PATENT DOCUMENTS

| | | | |
|---|---|---|---|
| 3,402,364 A | 9/1968 | De Lang | |
| 3,711,788 A | 1/1973 | Forkner | |
| 3,982,203 A | 9/1976 | De Wit | |
| 4,161,436 A | 7/1979 | Gould | |
| 4,525,034 A | 6/1985 | Simmons | |
| 4,677,639 A | 6/1987 | Sasser | |
| 4,740,986 A | 4/1988 | Reeder | |
| 4,746,201 A | 5/1988 | Gould | |

(Continued)

FOREIGN PATENT DOCUMENTS

EP 1 195 582 A1 4/2002

(Continued)

OTHER PUBLICATIONS

J. White, Long Optical Paths of Large Aperture, 32 *J. Opt. Soc. Amer.*, 285, May 1942.

(Continued)

*Primary Examiner*—Richard A. Rosenberger
(74) *Attorney, Agent, or Firm*—RatnerPrestia

(57) ABSTRACT

An apparatus and method for controlling a light source used in Cavity Ring-Down Spectroscopy. The apparatus comprises a controller that generates a control signal to activate and deactivate the light source based on a comparison of an energy signal from a resonant cavity and a threshold. The light source is activated for a time period based on the stabilization time of the light source and the time necessary to provide sufficient energy to the resonant cavity. Thereafter the controller deactivates the light source for a predetermined time period by interrupting its current source so that the light energy in the cavity rings down and so that the presence of analyte can be measured. The light energy from the light source is directly coupled to the resonant cavity from the light source.

38 Claims, 7 Drawing Sheets

U.S. PATENT DOCUMENTS

| | | | |
|---|---|---|---|
| 5,276,548 | A | 1/1994 | Margalith |
| 5,463,493 | A | 10/1995 | Shah |
| 5,483,342 | A | 1/1996 | Rockwell |
| 5,528,040 | A | 6/1996 | Lehmann |
| 5,835,231 | A | 11/1998 | Pipino |
| 5,912,740 | A | 6/1999 | Zare et al. |
| 6,233,052 | B1 * | 5/2001 | Zare et al. .................. 356/437 |
| 6,466,322 | B1 * | 10/2002 | Paldus et al. ............... 356/437 |

FOREIGN PATENT DOCUMENTS

| | | |
|---|---|---|
| JP | 63013386 | 1/1988 |

OTHER PUBLICATIONS

D. Heriott et al., Off-Axis Paths In Spherical Mirror Interferometers, 3 *Appl. Opt.* (4), 523, Apr. 1964.

A. O'Keefe, D. Deacon, Cavity Ring-Down Optical Spectrometer for Absorption Measurements Using Pulsed Laser Sources, 59 *Rev. Sci Instrum.*, 2544, Dec. 1988.

D. Romanini, K. Lehmann, Ring-Down Cavity Absorption Spectroscopy of the Very Weak HCN Overtone Bands with Six, Seven, and Eight Stretching Quanta, 99 *J. Chem. Phys.* (9), 6287, Nov. 1, 1993.

G. Rempe et al., Measurement of Ultralow Losses in an Optical Interferometer, 17 *Opt. Letters* (5), 363, Mar. 1, 1992.

T. Yu, M. Lin, Kinetics of Phenyl Radical Reactions Studied by the "Cavity-Ring-Down" Method, 115 *J. Am. Chem. Soc.*, 4371, 1993.

G. Meijer et al., Coherent Cavity Ring Down Spectroscopy, 217 *Chemical Physics Letters* (1, 2) 12, Jan. 7, 994.

J. Scherer et al., Cavity Ring Down Dye Laser Spectroscopy of Jet-Cooled Metal Clusters: $CU_2$ and $CU_3$, 172 *Chemical Physics Letters* (3, 4) 214, Sep. 7, 1990.

F. Stoelkel, G. Atkinson, Time Evolution of a Broadband Quasi-cw Dye Laser: Limitation of Sensitivity in Intracavity Laser Spectroscopy, 24 *Applied Optics* (21), 3591, Nov. 1, 1985.

K. Lehmann, D. Romanini, Molecules in the Stellar Environment, *Experimental Measurement of Weak Band Intensities in Molecules in the Stellar Environment*, Springer, 994.

G. Gould et al., Crossed Roof Prism Interferometer, 1 *Applied Optics* (4), 533, Jul. 1962.

A. Pipino et al., Evanescent Wave Cavity Ring-Down Spectroscopy with a Total-Internal Reflection Minicavity, 68 (8) *Rev. Sci. Instrum.*, 2978, Aug. 1997.

Dana Z. Anderson, Josef C. Frisch, Carl S. Masser, Mirror reflectometer based on optical cavity decay time, *Applied Optics*, vol. 23 No. 8, pp. 1238-1245, Apr. 15, 1984.

* cited by examiner

SYSTEM AND METHOD FOR CONTROLLING A LIGHT SOURCE FOR CAVITY RING-DOWN SPECTROSCOPY

This application is a Continuation-in-Part of application Ser. No. 10/145,209 filed on May 13, 2002 now abandoned.

FIELD OF THE INVENTION

This invention relates generally to absorption spectroscopy and, in particular, is directed to the activation and deactivation of a light source for use with an optical resonator for cavity ring-down spectroscopy.

BACKGROUND OF THE INVENTION

Referring now to the drawing, wherein like reference numerals refer to like elements throughout, FIG. 1 illustrates the electromagnetic spectrum on a logarithmic scale. The science of spectroscopy studies spectra. In contrast with sciences concerned with other parts of the spectrum, optics particularly involves visible and near-visible light—a very narrow part of the available spectrum which extends in wavelength from about 1 mm to about 1 nm. Near visible light includes colors redder than red (infrared) and colors more violet than violet (ultraviolet). The range extends just far enough to either side of visibility that the light can still be handled by most lenses and mirrors made of the usual materials. The wavelength dependence of optical properties of materials must often be considered.

Absorption-type spectroscopy offers high sensitivity, response times on the order of microseconds, immunity from poisoning, and limited interference from molecular species other than the species under study. Various molecular species can be detected or identified by absorption spectroscopy. Thus, absorption spectroscopy provides a general method of detecting important trace species. In the gas phase, the sensitivity and selectivity of this method is optimized because the species have their absorption strength concentrated in a set of sharp spectral lines. The narrow lines in the spectrum can be used to discriminate against most interfering species.

In many industrial processes, the concentration of trace species in flowing gas streams and liquids must be measured and analyzed with a high degree of speed and accuracy. Such measurement and analysis is required because the concentration of contaminants is often critical to the quality of the end product. Gases such as $N_2$, $O_2$, $H_2$, Ar, and He are used to manufacture integrated circuits, for example, and the presence in those gases of impurities—even at parts per billion (ppb) levels—is damaging and reduces the yield of operational circuits. Therefore, the relatively high sensitivity with which water can be spectroscopically monitored is important to manufacturers of high-purity gases used in the semiconductor industry. Various impurities must be detected in other industrial applications. Further, the presence of impurities, either inherent or deliberately placed, in liquids have become of particular concern of late.

Spectroscopy has obtained parts per million (ppm) level detection for gaseous contaminants in high-purity gases. Detection sensitivities at the ppb level are attainable in some cases. Accordingly, several spectroscopic methods have been applied to such applications as quantitative contamination monitoring in gases, including: absorption measurements in traditional long pathlength cells, photoacoustic spectroscopy, frequency modulation spectroscopy, and intracavity laser absorption spectroscopy. These methods have several features, discussed in U.S. Pat. No. 5,528,040 issued to Lehmann, which make them difficult to use and impractical for industrial applications. They have been largely confined, therefore, to laboratory investigations.

In contrast, continuous wave-cavity ring-down spectroscopy (CW-CRDS) has become an important spectroscopic technique with applications to science, industrial process control, and atmospheric trace gas detection. CW-CRDS has been demonstrated as a technique for the measurement of optical absorption that excels in the low-absorbance regime where conventional methods have inadequate sensitivity. CW-CRDS utilizes the mean lifetime of photons in a high-finesse optical resonator as the absorption-sensitive observable.

Typically, the resonator is formed from a pair of nominally equivalent, narrow band, ultra-high reflectivity dielectric mirrors, configured appropriately to form a stable optical resonator. A laser pulse is injected into the resonator through a mirror to experience a mean lifetime which depends upon the photon round-trip transit time, the length of the resonator, the absorption cross section and number density of the species, and a factor accounting for intrinsic resonator losses (which arise largely from the frequency-dependent mirror reflectivities when diffraction losses are negligible). The determination of optical absorption is transformed, therefore, from the conventional power-ratio measurement to a measurement of decay time. The ultimate sensitivity of CW-CRDS is determined by the magnitude of the intrinsic resonator losses, which can be minimized with techniques such as superpolishing that permit the fabrication of ultralow-loss optics.

FIG. 2 illustrates a conventional CW-CRDS apparatus 200. As shown in FIG. 2, light is generated from a narrow band, tunable, continuous wave diode laser 202. Laser 202 is temperature tuned by a temperature controller (not shown) to put its wavelength on the desired spectral line of the analyte. An acousto-optic modulator (AOM) 204 is positioned in front of and in line with the radiation emitted from laser 202. AOM 204 provides a means for providing light 206 from laser 202 along the optical axis 219 of resonant cavity 218. Light 206 exits AOM 204 and is directed by mirrors 208, 210 to cavity mirror 220 as light 206a. Light travels along optical axis 219 and exponentially decays between cavity mirrors 220 and 222. The measure of this decay is indicative of the presence or lack thereof of a trace species. Detector 212 is coupled between the output of optical cavity 218 and controller 214. Controller 214 is coupled to laser 202, processor 216, and AOM 204. Processor 216 processes signals from optical detector 212 in order to determine the level of trace species in optical resonator 218.

In AOM 204, a pressure transducer (not shown) creates a sound wave that modulates the index of refraction in an active nonlinear crystal (not shown), through a photoelastic effect. The sound wave produces a Bragg diffraction grating that disperses incoming light into multiple orders, such as zero order and first order. Different orders have different light beam energy and follow different beam directions. In CW-CRDS, typically, a first order light beam 206 is aligned along with optical axis 219 of cavity 218 incident on the cavity in-coupling mirror 220, and a zero order beam 224 is idled with a different optical path (other higher order beams are very weak and thus not addressed). Thus, AOM 204 controls the direction of beams 206, 224.

When AOM 204 is on, most light power (typically, up to 80%, depending on size of the beam, crystals within AOM 204, alignment, etc.) goes to the first order along optical axis 219 of resonant cavity 218 as light 206. The remaining beam power goes to the zero order (light 224), or other higher orders. The first order beam 206 is used for the input coupling light source; the zero order beam 224 is typically idled or used for diagnostic components. Once light energy is built up within the cavity, AOM 204 is turned off. This results in all the beam power going to the zero order as light 224, and no light 206 is coupled into resonant cavity 218. The stored light energy inside the cavity follows an exponential decay (ring down).

In order to "turn off" the laser light to optical cavity 218, and thus allow for energy within optical cavity 218 to "ring down," AOM 204, under control of controller 214 and through control line 224, redirects (deflects) light from laser 204 along path 224 and, thus, away from optical path 219 of optical resonator 218. This conventional approach has drawbacks, however, in that there are losses of light energy primarily through the redirecting means contained within the AOM. Other losses may also be present due to mirrors 208, 210 used to direct light from AOM 204 to optical cavity 218. It is estimated that only 50%-80% of light emitted by laser 202 eventually reaches optical resonator 218 as light 206a due to these losses. Furthermore, these conventional systems are costly and the AOM requires additional space and AOM driver (not shown) within the system.

To overcome the shortcomings of conventional systems, an improved system and method for providing and controlling laser light to a resonant cavity is provided. An object of the present invention is to replace the conventional AOM/control system with a simplified and cost effective control system.

SUMMARY OF THE INVENTION

To achieve that and other objects, and in view of its purposes, the present invention provides an improved apparatus and method for controlling a light source for use with a resonant cavity. The apparatus includes a controller for receiving a comparison of a detection signal and a predetermined threshold, the comparator generating a control signal to one of activate and deactivate the light source based on the comparison; a first delay circuit coupled to the controller for generating a first delay signal to the controller; and a second delay circuit coupled to the comparator and the controller for generating a second delay signal to the controller based on the comparison of the detection signal and the predetermined threshold.

According to another aspect of the invention, the light source provides light as an input to the resonant cavity to measure the presence of an analyte in the resonant cavity.

According to a further aspect of the invention, light from the source is coupled to the resonant cavity by an optical fiber.

According to yet another aspect of the invention, a collimator couples the light into the resonant cavity.

According to still another aspect of the invention, a comparator generates an output signal to the controller based on a comparison of the detection signal and a predetermined threshold.

According to yet a further aspect of the invention, a detector is coupled between the output of the resonant cavity and the comparator, and generates a signal based on the light output from the resonant cavity.

According to another aspect of the invention, the light source is deactivated once the signal generated from the detector exceeds the level of the threshold voltage.

According to yet another aspect of the invention, the first delay circuit is activated on the deactivation of the light source.

According to yet another aspect of the invention, the second delay circuit allows for the stabilization of the light source after re-energizing prior to a new set of data being examined.

According to yet another aspect of the invention, the light source is activated after an end of the first delay period.

According to yet another aspect of the invention, after an end of the first delay period, the light source is activated and energy builds up within the cavity through the current modulation.

According to still another aspect of the invention, an analyte level present in the resonant cavity is measured during the first delay period.

According to yet a further aspect of the invention, the controller deactivates the light source by shunting a supply of current for the light source.

According to yet another aspect of the invention, the light source is a laser.

According to still a further aspect of the invention, an algorithm is used to set the threshold voltage through the use of a digital to analog converter. This algorithm is used to establish the best cavity signal to noise ratio.

The method includes the steps of, detecting a light energy signal output from the resonant cavity; comparing the detected signal with a predetermined threshold; generating a control signal to control the light source based on the comparison; generating a first delay signal to the controller; generating a second delay signal after the end of the first delay signal; providing a current modulation; and measuring a level of the analyte after an end of the second delay signal.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Figure 1:
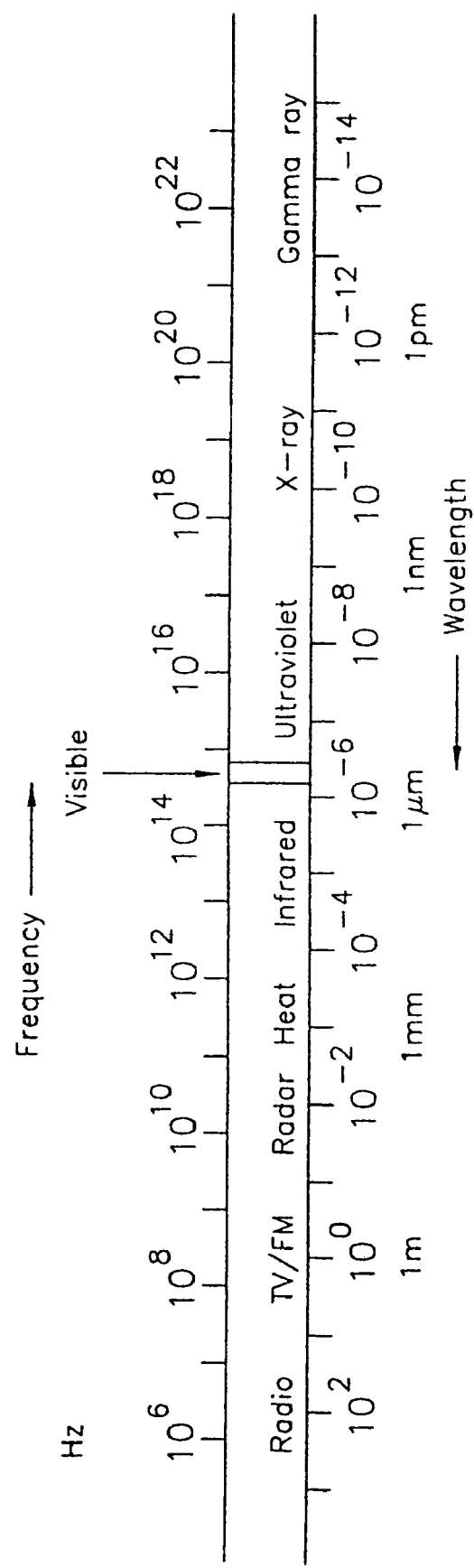
FIG. 1 illustrates the electromagnetic spectrum on a logarithmic scale.
Figure 2:
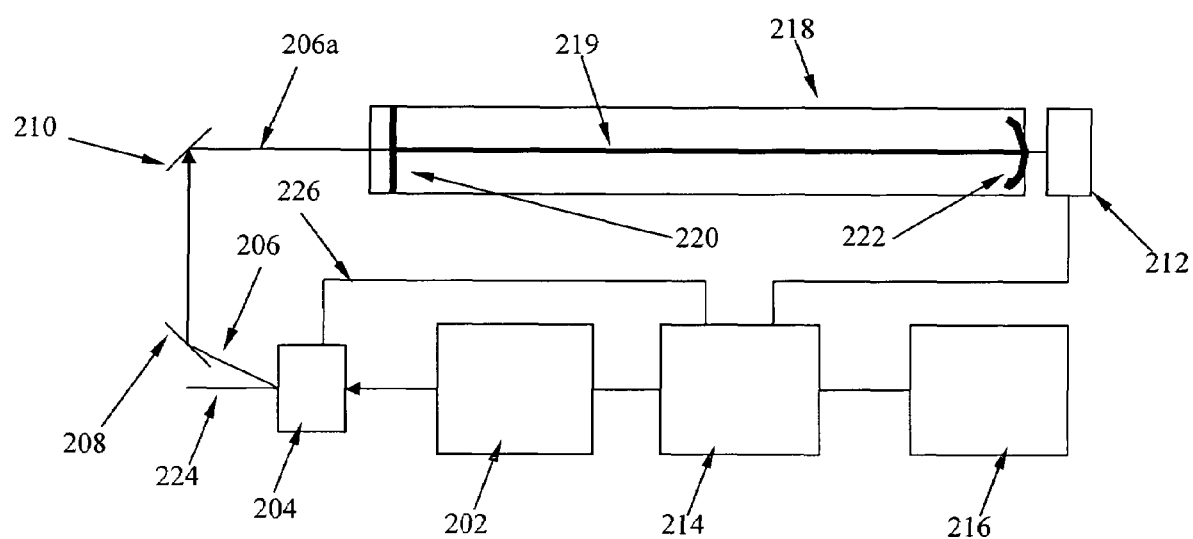
FIG. 2 illustrates a prior art CW-CRDS system.
Figure 3A:
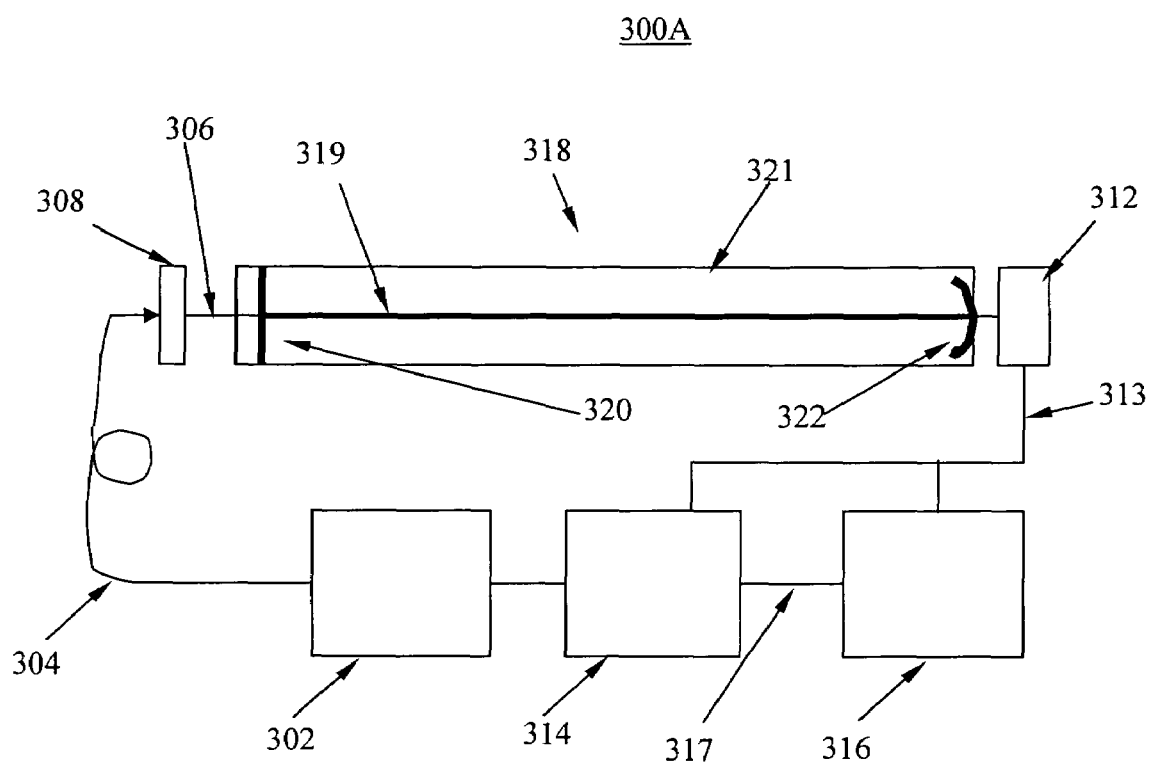
FIG. 3A illustrates an exemplary embodiment of the present invention.

FIG. 3A illustrates an exemplary embodiment of the present invention. As shown in FIG. 3A, light is generated from light source 302, such as a narrow band, tunable, continuous wave diode laser. Light source 302 is temperature tuned by a temperature controller (not shown) to put its wavelength on the desired spectral line of the analyte of interest. Light energy from light source 302 is coupled to fiber collimator 308 through optical fiber 304. Light energy 306 is, in turn, provided by collimator 308 to resonant cavity 318 and substantially parallel to its optical axis 319. Detector 312 is coupled to the output of optical cavity 318. In turn, detector 312 generates an output signal 313 and provides this signal to controller 314 and data analysis system 316. Controller 314 is coupled to light source 302 and data analysis system 316. Data analysis system 316, such as a personal computer or other specialized processor, processes signals 313 received from optical detector 312, in accordance with commands from controller 314, in order to determine the level of trace species (analyte) in optical resonator 318.

Desirably, light source 302 is a temperature and current controlled, tunable, narrow line-width radiation, semiconductor laser operating in the visible to near- and middle-infrared spectrum. Alternatively, light source 302 may be an external-cavity semiconductor diode laser.

Figure 3B:
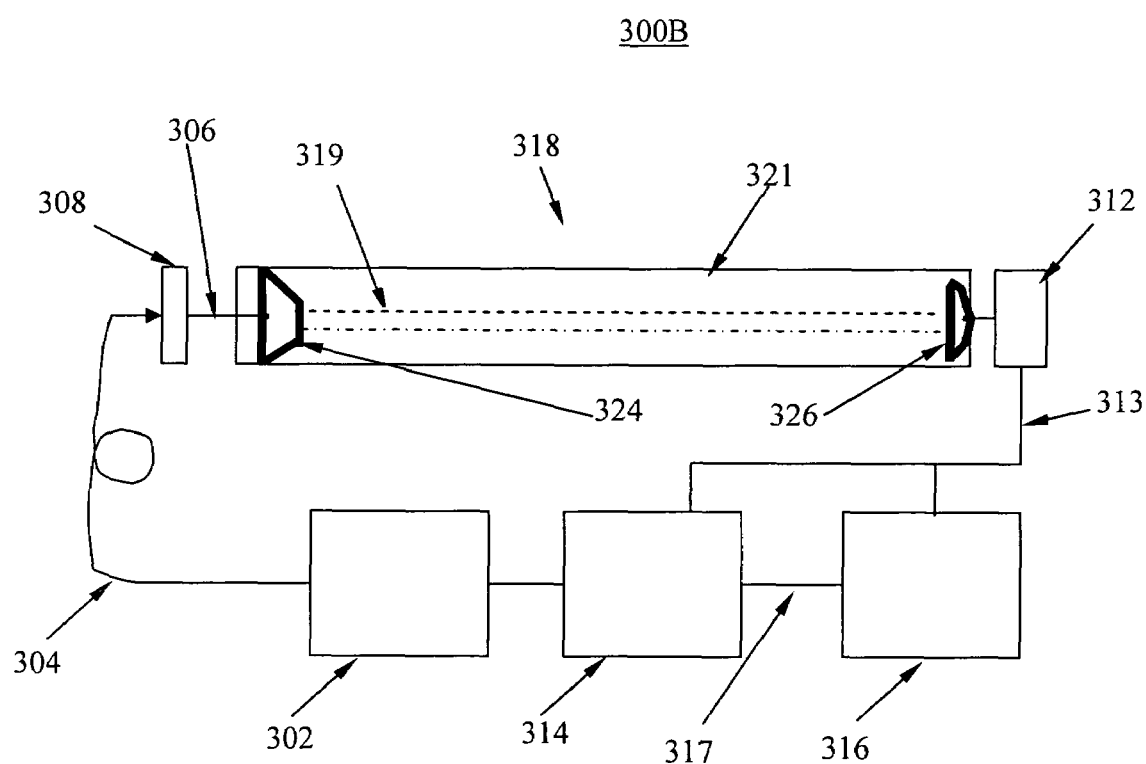
FIG. 3B illustrates another exemplary embodiment of the present invention.

Resonant cavity 318 desirably comprises at least a pair of high reflectivity mirrors 320, 322 and a gas cell 321 on which the mirrors are mounted. Cell 321 can be flow cell or vacuum cell, for example. Alternatively, and as shown in FIG. 3B, resonant cavity 318 may be comprised of a pair of prisms 324, 326 and a corresponding gas cell 321.

Detector 312 is desirably a photovoltaic detector, such as photodiodes or photo-multiplier tubes (PMT), for example.

Figure 4:
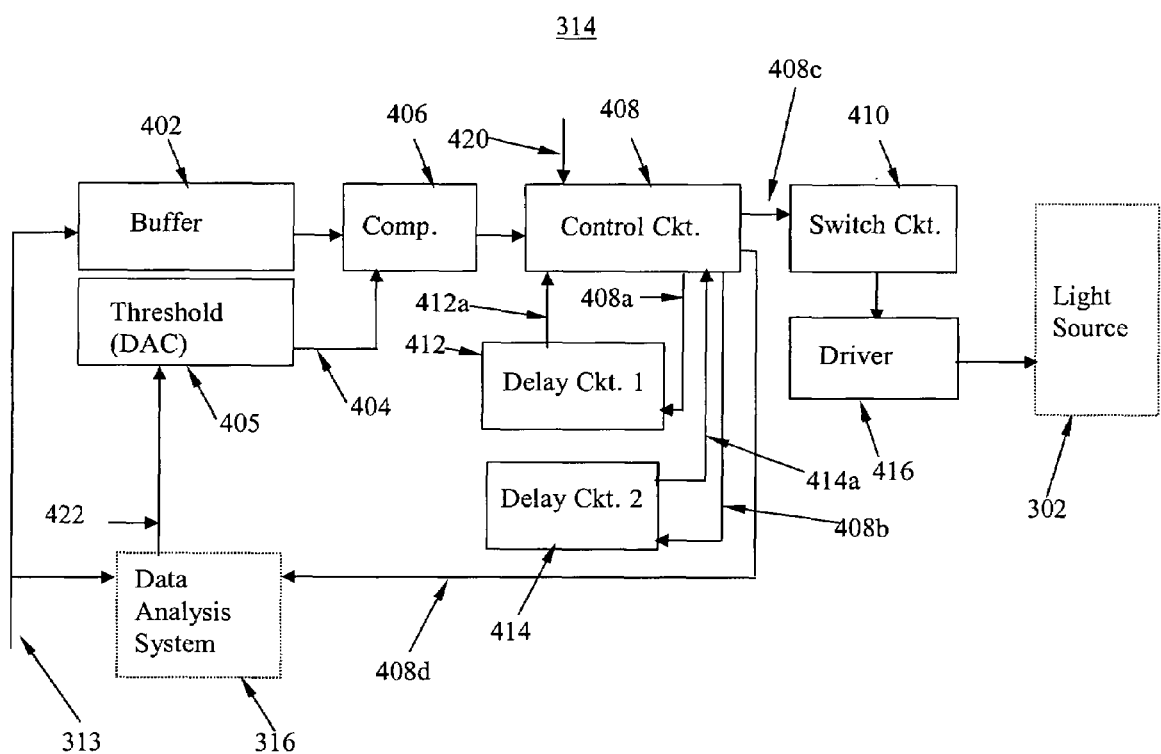
FIG. 4 is an illustration of an exemplary controller of the present invention.
Figure 6:
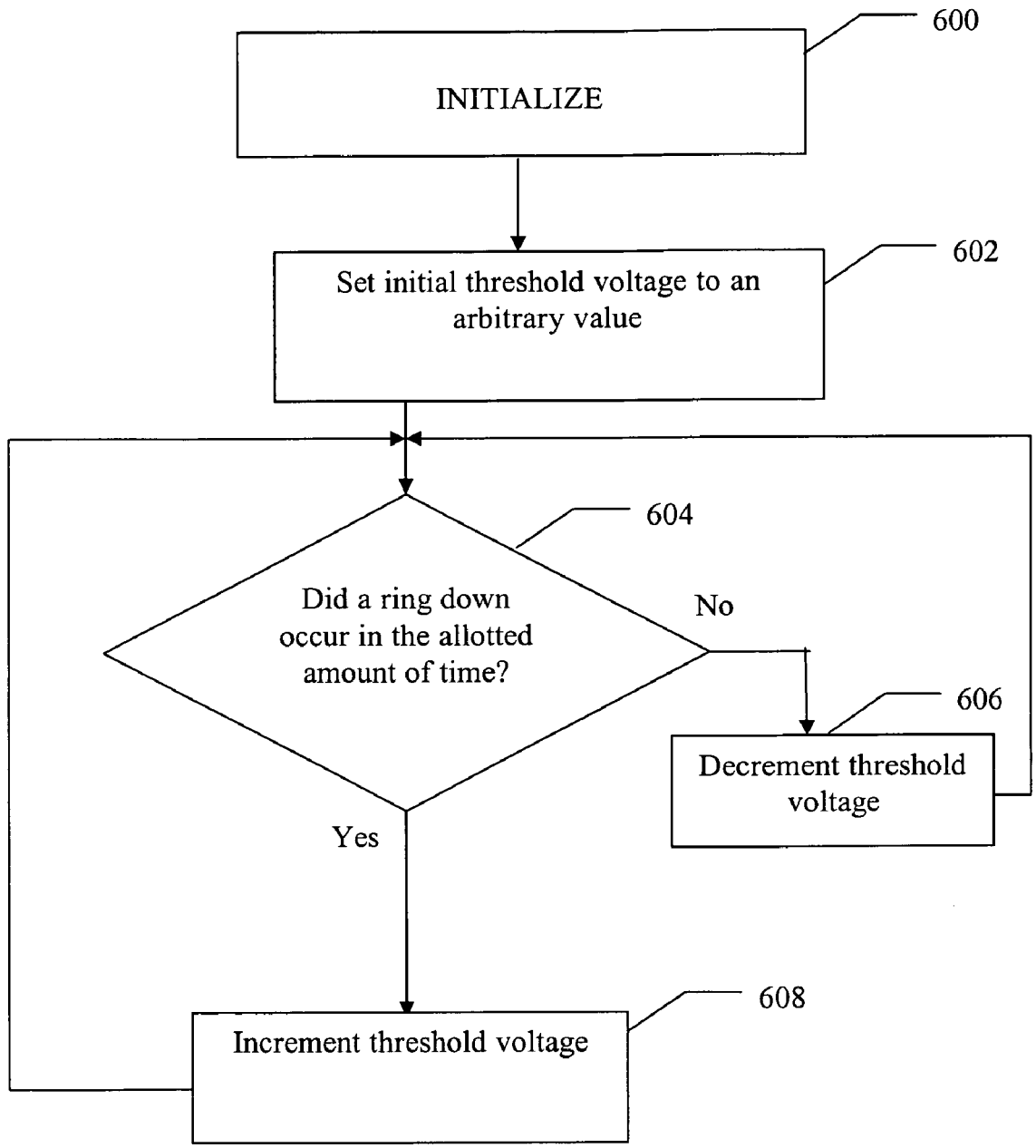
FIG. 6 is a flow chart according to an exemplary embodiment of the present invention.

Referring now to FIG. 4, a detailed block diagram of controller 314 is shown. As shown in FIG. 4, buffer 402 receives signal 313 (representing the ring down signal) from detector 312 (shown in FIGS. 3A-3B). Comparator 406 receives buffered signal 313 and performs a comparison with a threshold signal 404 generated by data analysis system 316 which, in one exemplary embodiment, is converted from a digital signal to an analog signal by threshold DAC 405. In operation, threshold signal 404 is incremented upward or downward to obtain the maximum signal level from detector 312. An exemplary process for this is illustrated in FIG. 6. As a result, threshold signal 404 is based on the level of the ring down signal which has the greatest signal to noise ratio. The output of comparator 406 is provided as an input to control circuit 408.

Referring now to FIG. 6, an exemplary flow chart for threshold control is illustrated. At Step 600, threshold control is initialized. This may be accomplished as part of system initialization or under control of Data Analysis System 316, for example. At Step 602, an initial threshold value is set. At Step 604, a determination is made whether a ring-down occurred within a predetermined time period, such as about one second, for example. If a ring-down occurred Step 608 is entered, otherwise Step 606 is entered. At Step 606, because a ring-down did not occur, the threshold voltage is decremented and Step 604 is re-entered. At Step 608, because a ring-down did occur, the threshold voltage is incremented and Step 604 is re-entered. This process is repeated as desired. In this way, an optimum signal to noise ratio is obtained.

Figure 5A:
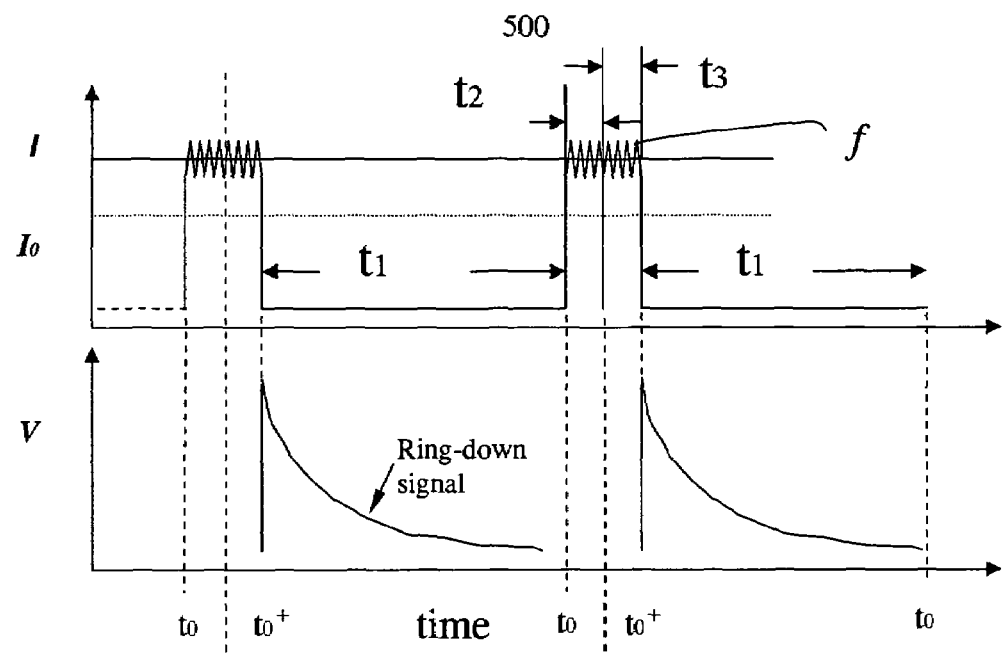
FIG. 5A is a graph illustrating various delay timing according to an exemplary embodiment of the present invention.

At time $t_0^+$, control circuit 408 generates control signal 408a, based on the rise of the ring down signal crossing the threshold level, in order to activate first delay circuit 412 (via control signal 408a) while simultaneously turning off light source 302 through switch circuit 410 and driver 416 (via control signal 408c). At the end of the first delay period $t_1$ (at subsequent time $t_0$ as shown in FIG. 5A), signal 412a is generated by first delay circuit 412 and provided to control circuit 408. In turn, control circuit 408 generates signal 408b to activate second delay circuit 414, and provides an active signal 408c (previously deactivated at the beginning of the first delay period) to switch circuit 410, which in turn activates light source 302 (shown in phantom and described above with respect to FIGS. 3A and 3B). At the end of delay period $t_2$ (shown in FIG. 5A), second delay circuit 414 generates signal 414a and provides it to control circuit 408 to indicate that light source 302 has stabilized and to begin a third time period $t_3$ (shown in FIG. 5A). Time period $t_3$ (described in detail below with respect to FIG. 5A) is used to ensure that resonant cavity 318 is fully charged through current modulation with light energy prior to measuring analyte concentration. At the end of time period $t_3$, which it should be noted is a time period such that cell 318 is sufficiently charged with light energy, control signal 408c is deactivated, which in turn is used by switch circuit 410 (and, in one exemplary embodiment, driver 416) to deactivate light source 302. In one embodiment of the present invention, switch circuit 410 shunts current from light source 302 using convention power devices to deactivate light source 302.

It should be noted that although terms such as active, inactive, activate, and/or deactivate as used, one of skill in that art will readily recognize and appreciate that the exemplary signal levels are arbitrary and may for example be inverted from those discussed. Further, although certain signals may be shown as maintaining a particular level throughout a particular time period, it is also possible that a level transition is all that may be required (such as a pulse) to accomplish the desired result.

Coincident with the deactivation of signal 408c, signal 408d is also generated and provided to data analysis system 316 (shown in phantom and described above with respect to FIGS. 3A and 3B). Although signal 408c and 408d are shown as separate signals, it may be preferable to combine them into a single control signal if desired. In such an approach conditioning of signal 408c may be required to provide a convenient control signal logic level (based on digital signals, for example) to provide proper control of data analysis system 316.

Figure 5B:
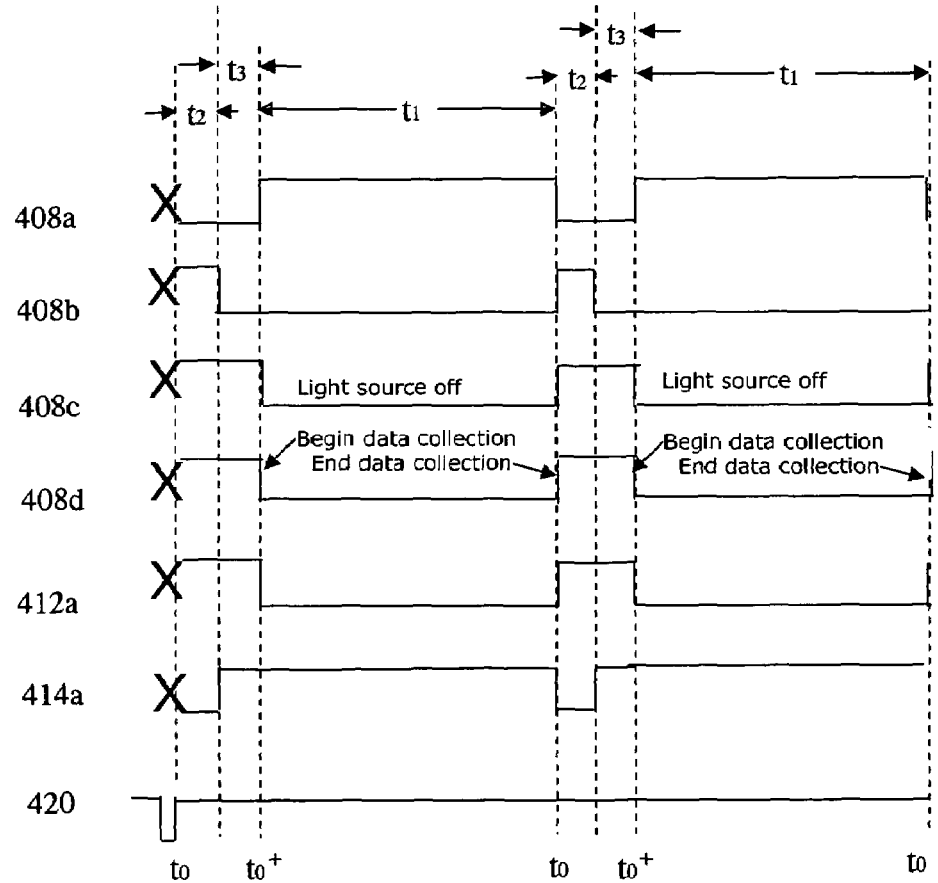
FIG. 5B is a partial timing diagram of certain signals according to an exemplary embodiment of the present invention.

Signal 408d (in the two-signal 408c/408d approach) is used by data analysis system 316 to indicate that light source 302 has been deactivated and that the measurement of the analyte should begin. In other words, during the period that control signal 408d is inactive data analysis system 316 is prevented from accepting new data represented by signal 313. At this point, the process repeats itself to measure successive ring downs by once again initializing first delay circuit 412 through control circuit 408. FIG. 5B illustrates an exemplary timing diagram for various ones of the aforementioned control signals.

Table 1 lists system status at various times set forth in FIG. 5A.

TABLE 1

| TIME | STATUS |
|---|---|
| Initial $t_0$ | Light source ON; Delay circuits OFF; Wait State |
| $t_0^+$ | Sufficient energy build up in resonant cavity; Activate first delay circuit; Turn off light source; |
| Subsequent $t_0$ | End of $t_1$ delay period; Turn on Light Source; Begin time delay $t_2$; (Cycle repeats) |

Because the above description relates to ongoing measurement of analytes, the circuit needs to be initialized prior to the first measurement. To accomplish this initialization, an initialization signal 420 may be provided as an input to control circuit 408. Upon activation of initialization signal 420, such as through a button, control signal from data analysis system 316, or an automatic reset at power-up, for example, delay time $t_0$ begins. The process then follows the procedure outlined above.

In one exemplary embodiment, switch circuit 410 functions as a current switch/shunt for enabling/disabling current drive to light source 302.

As a result, controller 314 energizes light source 302 to generate energy into resonant cavity 318, employs a first delay to allow light energy from light source 302 to completely ring down and be captured by data analysis system 316. A second delay then allows light source 302 to stabilize before looking for new data. Once sufficient energy is built up in resonant cavity 318 the process is repeated for a single wavelength ring-down data at a given temperature. Ring-down spectra are processed by the data analysis system 316. These various delays are illustrated in FIG. 5A.

As shown in FIG. 5A, at time $t_0$, light source 302 is energized by providing operating current I, which is above the light source's threshold current $I_0$. Threshold current $I_0$ varies based on the type of light source used. Delay time $t_2$ represents the delay to allow the light source to stabilize. In one exemplary embodiment, time delay $t_2$ is set to about 100 msec. Wait time $t_3$ represents the time to allow the current modulation to build up within resonant cavity 318. It should be noted that the actual time required for the current modulation to build up within resonant cavity 318 is <<t3.

In an exemplary embodiment, wait time $t_3$ is based on the modulation frequency f of light source 302, and is desirably equal to about 1/f. In another exemplary embodiment, t3 is equal to about 1/f plus the time needed to exceed the threshold level in the resonant cavity for a ring-down to occur. Time delay $t_1$ is based on the ring down time of resonant cavity 318. In order to allow sufficient time for light energy to "ring down" in resonant cavity 318, time delay $t_1$ is desirably set to about ten (10) times the ring down time of the cavity.

Laser temperature driver 416, under control of convention means (not shown), provides temperature control for light source 302 for the generation of a desired light frequency at a given temperature. The frequency is selected based on the particular analyte of interest.

Various advantages are realized from the present invention, such as:
- Allowing use of almost 100% of the beam power generated by light source 302 (there may be negligible albeit undetectable losses within optical fiber 304 and collimator 308). Higher intra-cavity energy build-up provides better signal to noise ratio and reduces shot noise. This is extremely beneficial when a light source is weak. As mentioned above, typically, only about 50~80% of light power goes to the first order when light passes through an AOM.
- Cost savings are realized from eliminating the AOM. A typically commercially available AOM costs approximately $2,000.
- Simplified CW-CRDS setup—This allows more spatial flexibility for the setup arrangements, and eliminates the mechanical and optical sensitivity, introduced by the AOM, to the testing environment.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. An apparatus for controlling a light source for use with a resonant cavity, the apparatus comprising:
   a detector coupled to an output of the resonant cavity, the detector generating a detection signal;
   a threshold generator for generating a threshold signal based on a first output signal from the resonant cavity;
   a comparator coupled to the detector and the threshold generator and receiving the detection signal and the threshold signal as inputs, the comparator generating a second output signal based on a comparison of the detection signal and the threshold signal;
   a controller coupled to the comparator for receiving the output signal from the comparator, the controller generating a control signal to at least one of activate and deactivate the light source based on the comparison;
   a first delay circuit coupled to the controller for generating a first delay signal to the controller responsive to the control signal; and
   a second delay circuit coupled to the controller for generating a second delay signal to the controller to allow the light source to stabilize before new data is accepted.

2. The apparatus according to claim 1, wherein the controller is initialized by an initialization signal.

3. The apparatus according to claim 1, wherein the light source provides light as an input to the resonant cavity used to measure the presence of an analyte in the resonant cavity.

4. The apparatus according to claim 1, wherein light from the source is coupled to the resonant cavity by an optical fiber.

5. The apparatus according to claim 4, further comprising a fiber collimator coupled between the optical fiber and an input of the resonant cavity.

6. The apparatus according to claim 1, wherein the light source is deactivated during a first delay period.

7. The apparatus according to claim 6, wherein the first delay period is based on a ring down time period of the resonant cavity.

8. The apparatus according to claim 7, wherein the first delay period is about 10 times the ring down period.

9. The apparatus according to claim 6, wherein the light source is activated after an end of the first delay period.

10. The apparatus according to claim 6, wherein an analyte level present in the resonant cavity is measured during the first delay period.

11. The apparatus according to claim 6, wherein the first delay period begins after a ring down signal crosses a predetermined threshold voltage.

12. The apparatus according to claim 11, wherein a third delay period is based on a modulation frequency of the light source and an energy level in the resonant cavity exceeding the threshold voltage level.

13. The apparatus according to claim 12, wherein a second delay period is based on a stabilization time of the light source.

14. The apparatus according to claim 13, wherein the second delay period is about 100 msec.

15. The apparatus according to claim 13, wherein the third delay period follows the second delay period.

16. The apparatus according to claim 11, wherein a third delay period is based on an inverse of a modulation frequency of the light source and an energy level in the resonant cavity exceeding the threshold voltage level.

17. The apparatus according to claim 11, wherein light energy builds up within the resonant cavity during the third delay period.

18. The apparatus according to claim 1, wherein the light source is a laser.

19. The apparatus according to claim 1, wherein the controller deactivates the light source by shunting a supply of current for the light source.

20. The apparatus according to claim 1, further comprising an optical fiber coupling light energy from the light source to the resonant cavity.

21. The apparatus according to claim 20, further comprising a fiber collimator coupled between an end of the optical fiber and the resonant cavity.

22. The apparatus according to claim 1, wherein the controller i) activates the light source at a time $t_0$ substantially coincident with termination of a first delay period $t_1$ such that—energy in the resonant cavity which will exceed a threshold voltage and ii) then deactivates the light source at a time $t_{0+}$ substantially coincident with termination of a third delay period $t_3$.

23. The apparatus according to claim 22, wherein the light source is active during a second delay period $t_2$ which is based on a stabilization time of the light source.

24. The apparatus according to claim 23, wherein the second delay period is further based on a modulation frequency of the light source along with the time period to allow sufficient energy to build in the cell which will exceed the threshold voltage.

25. The apparatus according to claim 1, wherein the threshold signal is one of decremented or incremented based on a level of previous ring-down signal.

26. The apparatus according to claim 1, wherein the output signal from the resonant cavity is a ring-down signal.

27. The apparatus according to claim 1, wherein the first delay signal has a duration sufficient to allow the output signal from the resonant cavity to dissipate and the second delay signal has a duration at least as great as a stabilization period of the light source.

28. A method for use with a light source and a resonant cavity to measure the presence of an analyte in a liquid or gas, the method comprising the steps of:
    detecting a light energy signal output from the resonant cavity;
    generating a threshold signal based on an amplitude of the signal output from the resonant cavity;
    comparing the detected signal with the threshold signal;
    generating a control signal to at least one of activate and deactivate the light source based on the comparison;
    generating a first delay signal to the controller, the first delay signal used to allow the output signal from the resonant cavity to dissipate;
    generating a second delay signal after an end of a first delay period, the second delay signal used to initiate a second delay period; and
    measuring a level of the analyte after an end of a first delay period, said analyte representative of the presence of a contaminant in the liquid or gas.

29. The method according to claim 28, further comprising the steps of:
    activating the light source coincident with generation of the second delay signal; and
    deactivating the light source during at least the first delay period.

30. The method according to claim 28, further comprising the step of providing an initialization signal to initialize the first delay signal.

31. The method according to claim 28 wherein the step of generating the threshold signal further comprising the steps of:
    incrementing or decrementing the threshold signal to obtain an optimum signal to noise ratio of the ring-down signal.

32. The method according to claim 28, wherein the second delay period is at least as great as a stabilization period of the light source.

33. A system for measuring the presence of an analyte in a resonant cavity, the system comprising of:
    detecting means for detecting a light energy signal output from the resonant cavity and generating a detector signal;
    threshold generating means for generating a threshold signal based on the output signal from the resonant cavity and a signal to noise ratio of the detector signal;
    comparison means for comparing the detected signal with the threshold signal;
    control means for generating a control signal to at least one of activate and deactivate the light source based on the comparison;
    first delay means for generating a first delay signal to the control means and initiating a first delay period responsive to the control signal;
    second delay means for generating a second delay signal and initiating a second delay period after an end of the first delay period; and
    processing means for measuring a level of the analyte after an end of the first delay period.

34. The system according to claim 33, wherein said processing means measures the level of analyte during said first delay period.

35. An apparatus for controlling a light source for use in cavity ring-down spectroscopy, the apparatus comprising:
    a controller for receiving a comparison of a detection signal and a predetermined threshold signal, the controller generating a control signal to at least one of activate and deactivate the light source based on the comparison;
    a first delay circuit coupled to the controller for generating a first delay signal to the controller, the first delay signal having a period during which the light source is deactivated; and
    a second delay circuit coupled to the controller for generating a second delay signal to the controller based on the completion of the first delay period, the light source being activated during at least a duration of the second signal.

36. An apparatus for controlling a light source for use with a resonant cavity, the apparatus comprising:
    a controller coupled to the comparator and the light source for receiving an output signal from the resonant cavity, the controller generating a control signal to at least one of activate and deactivate the light source based on the output signal from the resonant cavity;
    a first delay circuit coupled to a first input of the controller for receiving a control signal from the controller and generating a first delay signal to the controller responsive to the control signal, the first delay signal having a first predetermined time period; and
    a second delay circuit coupled to a further input of the controller for generating a second delay signal to the controller at an end of the first predetermined time period, the second delay signal having a second predetermined time period.

37. The apparatus according to claim 36, wherein the first predetermined time period is a period at least as great as a time necessary to allow the output signal from the resonant cavity to dissipate.

38. The apparatus according to claim 36, wherein the second predetermined time period is related to an inverse of a modulation frequency of the light source.

* * * * *